United States Patent [19]

Hartung et al.

[11] Patent Number: 5,302,323
[45] Date of Patent: Apr. 12, 1994

[54] SELENIUM SULFIDE SHAMPOO WITH CONDITIONING PROPERTIES

[75] Inventors: Donald E. Hartung, Arlington Heights, Ill.; Murray J. Sibley, Westerville, Ohio

[73] Assignee: Abbott Laboratories, Abbott Park, Ill.

[21] Appl. No.: 889,880

[22] Filed: May 29, 1992

[51] Int. Cl.$^5$ ............................................. C11D 1/12
[52] U.S. Cl. ............................ 252/550; 252/174.15; 252/174.25; 252/174.17; 252/546; 252/DIG. 5; 252/DIG. 13; 424/70; 424/702; 424/DIG. 4
[58] Field of Search .................. 252/174.15, 174.25, 252/174.17, 546, 550, DIG. 5, DIG. 13; 424/70, 702, DIG. 4

[56] References Cited

U.S. PATENT DOCUMENTS

| | | | |
|---|---|---|---|
| 4,854,333 | 8/1989 | Inman et al. | 424/70 |
| 4,927,563 | 5/1990 | McCall | 252/174.15 |
| 5,015,415 | 5/1991 | Goze et al. | 252/174.15 |
| 5,151,209 | 9/1992 | McCall et al. | 252/174.15 |

*Primary Examiner*—Paul Lieberman
*Assistant Examiner*—Necholus Ogden
*Attorney, Agent, or Firm*—Lonnie R. Drayer; Donald O. Nickey

[57] ABSTRACT

A novel anti-dandruff conditioning shampoo contains at least one suspending agent, and a buffer system, with the shampoo formulation having an active detergent content of at least 18%. Preferably the buffer system contains sodium citrate and citric acid. Preferably the shampoo contains two detergents with the two detergents being ammonium lauryl ether sulfate and ammonium lauryl sulfate. Preferably the shampoo contains two suspending agents with the two suspending agents being di(hydrogenated) tallow phthalic acid amide and a suspending agent selected from the group consisting of hydroxypropyl methylcellulose and magnesium aluminum silicate.

8 Claims, No Drawings

SELENIUM SULFIDE SHAMPOO WITH CONDITIONING PROPERTIES

TECHNICAL FIELD

The present invention relates generally to anti-dandruff shampoos with conditioner, and more particularly to such shampoos which also include a buffer system and have a certain level of detergent activity.

BACKGROUND ART

In modern society there is a great deal of emphasis on the appearance and manageability of hair. For example, over time, human hair acquires a dirty look and feel as a result of its contact with the atmosphere and as a result of sebum secreted by the head. Therefore, conformity with current societal norms requires that the hair be kept clean, and shampooed regularly. However, in practice, the tendency is for individuals to shampoo their hair daily.

Shampooing the hair cleans by removing excess soil and sebum. However, the shampooing process often leaves the hair in a tangled and generally unmanageable state. To improve the manageability of washed hair, conditioning aids were developed such as hair rinses. Initially such conditioning aids were applied to the hair following the step of shampooing the hair. However, there are disadvantages associated with such conditioning products.

With respect to hair rinses, they must remain on the hair for a length of time and then the hair must be rinsed with fresh water an additional time. With respect to leave-on hair conditioners, the amount of conditioner to apply is often difficult to determine based on the amount and thickness of the hair to be conditioned, and even then the uniform distribution of conditioner throughout the hair can be a problem. Therefore, to cope with the above problems it became desirable to formulate a combined shampoo and conditioner.

Although shampoos and conditioners in theory could be combined in the same product, in actuality problems arose concerning the compatibility between the detergents and the conditioners present in the product. This problem was addressed by the development of suspension agents. For example, U.S. Pat. No. 4,741,855 discloses a shampoo composition comprising a detergent, a silicone conditioner, water and a suspension agent, with choices for the suspension agent including long chain esters of ethylene glycol, and esters of long chain fatty amine oxides. However, the conditioning shampoo is not an anti-dandruff shampoo.

Still further, U.S. Pat. No. 5,015,415 discloses a conditioning shampoo comprising a certain phthalic acid and phthalic acid ammonium salts or mixtures thereof incorporated into a shampoo base with a silicone conditioner. In Cosmetics, Toiletry, and Fragrance Association (CTFA) nomenclature, phthalic acids may be designated as amido carboxy benzoic acids, and phthalic acid ammonium salts may be designated ammonium amido carboxy benzoates.

U.S. Pat. No. 4,927,563 discloses a selenium sulfide shampoo containing a mixture of xanthan gum and magnesium aluminum silicate as a suspending system. Still another known suspension system comprises xanthan gum, glycerol distearate and cetyl alcohol.

The entire matter encounters additional complications when the product is desired for use as an anti-dandruff conditioning shampoo. Typical anti-dandruff agents include colloidal or powder sulfur, coal tar derivatives, zinc pyrithione, selenium sulfide and mixtures thereof. With respect to selenium sulfide, its anti-dandruff effectiveness was established when U.S. Pat. No. 2,694,669 was awarded for an invention in a stabilized selenium disulfide therapeutic shampoo.

Although selenium sulfide is effective in controlling dandruff, its use in a shampoo, much less in a conditioning shampoo, creates additional problems. The first problem that is created concerns the stability of the shampoo. One of the constant concerns with a selenium sulfide shampoo is that the pH be kept below 6.5 during its shelf life. When the pH becomes greater than 6.5, the selenium sulfide starts to break down, with the result being that potentially toxic sulfides may be formed. The approach to that problem in the past has been to formulate the shampoo with a strongly acidic pH, and then hope that over the shelf life of the shampoo the pH does not drift above 6.5.

The second problem concerns the specific density of selenium sulfide. The high specific density of selenium sulfide makes it difficult for it to remain suspended in liquid shampoos. Selenium sulfide tends to precipitate out of solution. In the past it was found that two or more suspending agents often had to be used to overcome this problem. Examples of such suspension systems included ones comprising bentonite and magnesium aluminum silicate, or hydroxypropyl methylcellulose and magnesium aluminum silicate.

It is thus apparent that a need exists for an improved anti-dandruff conditioning shampoo containing selenium sulfide.

DISCLOSURE OF THE INVENTION

There is disclosed an anti-dandruff shampoo with conditioner comprising at least one detergent, a silicone compound conditioning agent, selenium sulfide, and at least one suspending agent, with the anti-dandruff shampoo with conditioner also comprising a buffer system and an active detergent content of at least 18%.

Preferably the selenium sulfide is present at a level of from about 0.5% to about 2.5% by weight. More preferably the selenium sulfide is present at a level of from about 0.8% to about 1.5% by weight. Most preferably the selenium sulfide is present at a level of 1.0% by weight.

Preferably the active detergent content of the anti-dandruff shampoo with conditioner is at a level of from about 18% to about 20% by weight. More preferably the active detergent content of the anti-dandruff shampoo with conditioner is at a level of 18.2% by weight. Additionally, the buffer system is comprised of sodium citrate and citric acid.

Preferably the shampoo of this invention has a pH value in the range of about 4.0 to about 6.5. More preferably the shampoo of this invention has a pH value in the range of about 5.0 to about 6.0. Furthermore, the shampoo of this invention more preferably comprises two detergents and two suspending agents. Most preferably the two detergents are ammonium lauryl ether sulfate and ammonium lauryl sulfate. Most preferably the two suspending agents are di(hydrogenated) tallow phthalic acid amide and a suspending agent selected from the group consisting of hydroxypropyl methylcellulose and magnesium aluminum silicate.

There is also disclosed an anti-dandruff shampoo with conditioner comprising two detergents, a silicone compound conditioning agent, selenium sulfide, two suspending agents, and a buffer system, with the anti-dandruff shampoo with conditioner having an active detergent content of at least 18% by weight.

In the preferred formulation of the invention the selenium sulfide is preferably present at a level of 1.0% by weight. The buffer system is preferably comprised of sodium citrate and citric acid. The shampoo of this invention preferably has a pH value in the range of about 4.0 to about 6.0. The two detergents are preferably ammonium lauryl ether sulfate and ammonium lauryl sulfate. The two suspending agents are preferably di(hydrogenated) tallow phthalic acid amide and a suspending agent selected from the group consisting of hydroxypropyl methylcellulose and magnesium aluminum silicate.

There is also disclosed an anti-dandruff shampoo with conditioner comprising two detergents, said two detergents being ammonium lauryl ether sulfate and ammonium lauryl sulfate, a silicone compound conditioning agent, selenium sulfide, two suspending agents, said two suspending agents being di(hydrogenated) tallow phthalic acid amide and a suspending agent selected from the group consisting of hydroxypropyl methylcellulose and magnesium aluminum silicate, and a buffer system, said shampoo having an active detergent content of at least 18% by weight and said shampoo having a pH value in the range of about 4.0 to about 6.0. The selenium sulfide is preferably present at a level of 1.0% by weight and said buffer system preferably comprises of sodium citrate and citric acid.

One aspect of the present invention provides an anti-dandruff conditioning shampoo that cleans and conditions hair while controlling dandruff.

Another aspect of the present invention is to provide a stable selenium sulfide conditioning shampoo.

Still another aspect of the invention provides an anti-dandruff conditioning shampoo containing selenium sulfide which produces ample lather.

Other aspects and advantages of the instant invention will be apparent from the following description, examples, and appended claims.

DETAILED DESCRIPTION OF THE INVENTION

The present invention is concerned with an anti-dandruff conditioning shampoo. The detergent component in most conditioning shampoos is an anionic surfactant, an example of which is ammonium lauryl sulfate. This shampoo ingredient is normally found in a liquid form as an aqueous solution. The actual detergent activity of a surfactant such as ammonium lauryl sulfate ranges from about 28% to about 30%. Thus it can be appreciated that a shampoo comprising 50% ammonium lauryl sulfate by weight would have a level of detergent activity in the range of about 14% to about 15%.

The preceding example is in fact close to the active detergent content of most shampoos. While most shampoos have an active detergent content in the range of from about 10% to about 15% by weight, it has been discovered that superior results can be achieved in anti-dandruff conditioning shampoos by having an active detergent content of at least 18% by weight. Additionally, it has been discovered that superior results can be achieved by the utilization of two anionic surfactants, namely ammonium lauryl sulfate and ammonium lauryl ether sulfate.

In choosing a conditioner to combine with the anionic surfactants found in most conditioning shampoos, a popular choice is a cationic conditioning agent, an example of which is tricetylammonium chloride. Some manufacturers of conditioning shampoos have chosen instead to use a conditioning agent which is neither anionic nor cationic, an example of such a conditioning agent being dimethicone.

Regardless of the choice of conditioner, the inclusion of selenium sulfide at a level of about 0.5% to about 2.5% by weight requires a highly effective suspension system.

At the high end of the preceding range of selenium sulfide concentration, the shampoo would probably have to be prescribed by a physician. Therefore more preferably the selenium sulfide content is at a level of about 0.8% to about 1.5% by weight, with the preferred embodiment of the invention comprising selenium sulfide at a level of about 1.0% by weight.

The conditioning shampoo of this invention utilizes a unique suspension system comprising two suspending agents, one of which is di(hydrogenated) tallow phthalic acid amide. It has been discovered that superior results can be achieved in anti-dandruff conditioning shampoos through the utilization of di(hydrogenated) tallow phthalic acid amide coupled with the use of either hydroxypropyl methylcellulose or magnesium aluminum silicate.

It has also been discovered that superior results can be achieved in an anti-dandruff conditioning shampoo by including a buffer system. The buffer system utilized in the preferred embodiment of this invention comprises sodium citrate and citric acid. While the pH of the shampoo of this invention preferably is in the range of about 4.0 to about 6.5, the presence of the buffer system more preferably permits the pH value to be in the range of about 5.0 to about 6.0.

In actual use, an anti-dandruff conditioning shampoo embodying this invention can be prepared having the formula set forth in Table I below.

TABLE I

| | CONCENTRATION BY WEIGHT | |
| --- | --- | --- |
| INGREDIENT | TARGET | ACCEPTABLE RANGE |
| Ammonium Lauryl Ether Sulfate | 15.0% | 12–18% |
| Ammonium Lauryl Sulfate | 50.0% | 45–55% |
| Citric Acid | 0.13% | 0–0.2% |
| Cocamide DEA | 1.0% | 0.5–2.0% |
| Dimethicone | 0.5% | 0.25–1.0% |
| Di(Hydrogenated) Tallow Phthalic Acid Amide | 5.0% | 2.5%–10.0% |
| DMDM Hydantoin | 0.2% | 0.2–0.4% |
| Fragrance | 0.5% | 0.25%–0.65% |
| Hydroxypropyl Methylcellulose | 0.3% | 0.2–0.5% |
| Selenium Sulfide | 1.0% | .9–1.1% |
| Sodium Citrate | 0.04% | 0–0.1% |
| Water | to 100.0% | to 100.0% |

The anti-dandruff conditioning shampoo of this invention is preferably prepared as follows. Twenty-two percent of the total water is maintained at between 60° and 65° C. The hydroxypropyl methylcellulose is then throughly wetted and dispersed in the heated water. The ammonium lauryl ether sulfate, di(hydrogenated) tallow phthalic acid amide and dimethicone are then added. The resultant mixture is then maintained to between 60° and 65° C. for at least 20 minutes, at which point in the formulation process heating is no longer necessary. It should be understood for purposes of the discussion of this invention that the CTFA designation for N,N-di(hydrogenated) tallow amido benzoic acid is used, namely di(hydrogenated) tallow phthalic acid amide.

Then, the ammonium lauryl sulfate, cocamide DEA, DMDM hydantoin, and selenium sulfide are added, with the selenium sulfide being added in a slurry form. The container from which the selenium sulfide is added is then rinsed with water to get all of the selenium sulfide into solution. The citric acid, sodium citrate and fragrance are then added, followed by more water if necessary.

The ammonium lauryl ether sulfate and ammonium lauryl sulfate are both water base anionic surfactants with a detergent activity of between 28% and 30%. This combination of anionic surfactants provides excellent lathering properties with all types of water. The cocamide DEA (coconut diethanolamide) assists in controlling the viscosity of the conditioning shampoo, as well as helping to stabilize the foam.

Dimethicone is a silicone conditioning agent. Di(hydrogenated) tallow phthalic acid amide acts as a suspending agent for the selenium sulfide, and may also impart some conditioning properties to the shampoo. DMDM hydantoin acts as a preservative, while any fragrance that is used is for aesthetic effect. The hydroxypropyl methyl cellulose is another suspending agent. The selenium sulfide is the anti-dandruff agent.

In actual use, an anti-dandruff conditioning shampoo made in accordance with this invention forms a rich, luxurious lather. Following shampooing the hair is clean and manageable. The shampoo, while gentle on the hair, provides excellent treatment for dandruff.

The invention will be better understood in view of the following examples, which are illustrative only and should not be construed as limiting the invention.

EXAMPLE I

A shampoo is prepared having the formulation set forth in Table 2.

TABLE 2

| INGREDIENT | CONCENTRATION BY WEIGHT |
| --- | --- |
| EDTA | 0.2% |
| STEPANOL AM-V (30%) | 50.0% |
| Citric Acid (50%) | Q.S. |
| NINOL CO-40 | 2.0% |
| Di(Hydrogenated) Tallow Phthalic Acid Amide | 5.0% |
| DMDM Hydantoin | 0.2% |
| Ammonium Chloride | Q.S. |
| Selenium Sulfide | 1.0% |
| Sodium Hydroxide (50%) | Q.S. |
| Water | to 100.0% |

The shampoo of Table 2 is prepared as follows. Into a suitable vessel equipped with mixing, heating and cooling capabilities is added water, EDTA, coconut diethanolamide (cocamide DEA) sold under the trademark NINOL CO-40, and ammonium lauryl sulfate sold under the trademark STEPANOL AM-V. NINOL CO-40 is a trademark of the Stepan Company, Northfield, Ill., U.S.A.. STEPANOL AM-V is also a trademark of the Stepan Company for an ammonium lauryl sulfate solution that is 27-29% active.

The solution is then agitated and heated. Next, selenium sulfide is added. At solution temperature about 60° C. di(hydrogenated) tallow phthalic acid amide is added. The solution is heated to between 70° and 75° C. where it then is agitated for an additional 30 minutes, and subsequently cooled. When the temperature of the solution reaches 50° C., DMDM hydantoin sold under the trademark GLYDANT is added. The pH is adjusted to a level of about 5.0 to about 5.4 with sodium hydroxide or citric acid. The viscosity may be adjusted if necessary with the ammonium chloride. The shampoo of Table 2 had an anionic surfactant content below 18% by weight, and the lathering, foaming and conditioning properties of this shampoo were not satisfactory. For each of the shampoos described herein the lathering properties were evaluated both in laboratory tests and "half-head" shampoo tests on persons.

EXAMPLE 2

A shampoo is prepared having the formulation set forth in Table 3.

TABLE 3

| INGREDIENT | CONCENTRATION BY WEIGHT |
| --- | --- |
| EDTA | 0.2% |
| STEPANOL AM-V (30%) | 25.0% |
| STEOL CA 460 (60%) | 15.0% |
| Citric Acid (50%) | Q.S. |
| NINOL CO-40 | 2.0% |
| Di(Hydrogenated) Tallow Phthalic Acid Amide | 5.0% |
| DMDM Hydantoin | 0.2% |
| Ammonium Chloride | Q.S. |
| Selenium Sulfide | 1.0% |
| Sodium Hydroxide (50%) | Q.S. |
| Water | to 100.0% |

The shampoo of Table 3 is prepared as follows. Into a suitable vessel equipped with mixing, heating and cooling capabilities is added water, EDTA, coconut diethanolamide (cocamide DEA) sold under the trademark NINOL CO-40, ammonium lauryl sulfate sold under the trademark STEPANOL AM-V, and ammonium lauryl ether sulfate sold under the trademark STEOL CA 460. NINOL CO-40 and STEOL CA 460 are trademarks of the Stepan Company. STEPANOL AM-V is also a trademark of the Stepan Company for an ammonium lauryl sulfate solution that is 27-29% active.

The solution is then agitated and heated. Next, selenium sulfide is added. At a solution temperature of about 60° C. di(hydrogenated) tallow phthalic acid amide is added. The solution is heated to between 70° and 75° C. where it then is agitated for an additional 30 minutes, and subsequently cooled. When the temperature of the solution reaches 50° C., DMDM hydantoin sold under the trademark GLYDANT is added. The pH is adjusted to a level of from about 5.0 to about 5.4 with the sodium hydroxide or citric acid. The viscosity may be adjusted if necessary with the ammonium chloride.

The initial (flash) foaming of the shampoo of Table 3 was better than the shampoo of Table 2, but overall foaming and conditioning still was not satisfactory.

With respect to shampoos having the formulations set forth in Tables 2 and 3, the anionic detergents in them and the coconut diethanolamide hydrolyze, with the resultant released by-products driving up the pH. As discussed above, the elevated pH could create a problem with the stability of the anti-dandruff shampoo formulation. Additionally, the shampoos made in accordance with the formulas of Tables 2 and 3 were void of conditioner. At this point it was decided that the shampoo formulation should include a buffer system to maintain the shampoo's pH in the range of 4 to 6.

EXAMPLE 3

A shampoo is prepared having the formulation set forth in Table 4.

TABLE 4

| INGREDIENT | CONCENTRATION BY WEIGHT |
| --- | --- |
| STEPANOL AM-V (30%) | 53.5% |
| Citric Acid (50%) | Q.S. |
| NINOL CO-40 | 2.0% |
| Di(Hydrogenated) Tallow Phthalic Acid Amide | 5.0% |
| DMDM Hydantoin | Q.S. |
| Ammonium Chloride | Q.S. |
| Selenium Sulfide | 1.0% |
| Water | to 100.0% |

The shampoo of Table 4 is prepared as follows. Into a suitable vessel equipped with mixing, heating and cooling capabilities is added water, coconut diethanolamide (coconut DEA) sold under the trademark NINOL CO-40, and ammonium lauryl sulfate sold under the trademark STEPANOL AM-V. NINOL CO-40 is a trademark of the Stepan Company. STEPANOL AM-V is also a trademark of the Stepan Company for an ammonium lauryl sulfate solution that is 27–29% active.

The solution is then agitated and heated. Next, selenium sulfide is added. At a solution temperature of about 60° C. di(hydrogenated) tallow phthalic acid amide is added. The solution is heated to between 70° and 75° C. where it then is agitated for an additional 30 minutes. The solution is then homogenized for 10 to 15 minutes at 75° C. or alternatively passed through a colloid mill. The solution is then cooled. When the temperature of the solution reaches 38° C., DMDM hydantoin is added. The pH is adjusted to a level of about 5.0 to about 6.2 with the citric acid. The viscosity may be adjusted if necessary with the ammonium chloride.

With respect to a shampoo having the formulation set forth in Table 4, the anionic detergent in them and the coconut diethanolamide hydrolyze, with the resultant released by-products driving up the pH. As discussed above, an elevated pH could create a problem with the stability of the anti-dandruff shampoo formulation. The shampoo made in accordance with the formula of Tables 4 was void of conditioner. Still further, the shampoo's lather was not as rich or luxurious as desired.

EXAMPLE 4

A shampoo is prepared having the formula set forth in Table 5.

TABLE 5

| INGREDIENT | CONCENTRATION BY WEIGHT |
| --- | --- |
| Ammonium Lauryl Ether Sulfate | 15.0% |
| Ammonium Lauryl Sulfate | 40.0% |
| Citric Acid | 0.13% |
| Coconut DEA | 0.5% |
| Dimethicone | 0.5% |
| Di(Hydrogenated) Tallow Phthalic Acid Amide | 5.0% |
| DMDM Hydantoin | 0.2% |
| Fragrance | 0.5% |
| Hydroxypropyl Methylcellulose | 0.3% |
| Selenium Sulfide | 1.0% |
| Sodium Citrate | 0.04% |
| Magnesium Aluminum Silicate | 1.0% |
| Water | to 100.0% |

The anti-dandruff conditioning shampoo of this formulation exhibits poor viscosity. Put another way, it is too runny when poured for shampooing. A shampoo according to the present invention has a viscosity of at least 3,000 centipoise as measured by a Brookfield viscometer. Also, when this formulation is used, the shampoo's lather is not as rich or luxurious as desired.

EXAMPLE 5

A shampoo embodying this invention can be prepared having the formula set forth in Table 6.

TABLE 6

| INGREDIENT | CONCENTRATION BY WEIGHT |
| --- | --- |
| Ammonium Lauryl Ether Sulfate | 15.0% |
| Ammonium Lauryl Sulfate | 50.0% |
| Citric Acid | 0.13% |
| Coconut DEA | 1.0% |
| Dimethicone | 0.5% |
| Di(Hydrogenated) Tallow Phthalic Acid Amide | 5.0% |
| DMDM Hydantoin | 0.2% |
| Fragrance | 0.5% |
| Magnesium Aluminum Silicate | 1.0% |
| Selenium Sulfide | 1.0% |
| Sodium Citrate | 0.04% |
| Water | to 100.0% |

In actual use, the anti-dandruff conditioning shampoo made in accordance with this formulation forms an acceptable, rich, luxurious lather. Following shampooing the hair is clean and left in a manageable condition. The shampoo, while gentle on the hair, provides excellent treatment for dandruff. However, the suspension system is not as efficient. The shampoo of Table 6 is, however, considered to be an alternative embodiment of the present invention.

While the anti-dandruff conditioning shampoo herein described constitutes a preferred embodiment of this invention, it is to be understood that the invention is not limited to this precise formulation and that changes may be made therein without departing from the scope of the invention which is defined in the appended claims.

What is claimed:

1. An anti-dandruff shampoo with conditioner comprising:
   (a) two detergents, said two detergents being ammonium lauryl ether sulfate and ammonium lauryl sulfate;
   (b) a silicone compound conditioning agent;
   (c) selenium sulfide;
   (d) two suspending agents, said two suspending agents being di(hydrogenated) tallow phthalic acid amide and hydroxypropyl methylcellulose said hydroxypropyl methylcellulose present at a level in the range of 0.2% to 0.5%; and
   (e) a buffer system, the shampoo having an active detergent content of at least 18% and a pH in the range of about 4.0 to about 6.0.

2. An anti-dandruff shampoo with conditioner according to claim 1 wherein said selenium sulfide is present at a level of 1.0% by weight and wherein said buffer system comprises sodium citrate and citric acid.

3. An anti-dandruff shampoo with conditioner with a pH value less than or equal to 6.5 comprising by weight about:

| INGREDIENT | CONCENTRATION BY WEIGHT |
| --- | --- |
| Ammonium Lauryl Ether Sulfate | 12–18% |
| Ammonium Lauryl Sulfate | 45–55% |
| Citric Acid | 0–0.2% |
| Cocamide DEA | 0.5–2.0% |
| Dimethicone | 0.25–1.0% |
| Di(Hydrogentated) Tallow Phthalic Acid Amide | 2.5%–10.0% |
| DMDM Hydantoin | 0.2–0.4% |
| Fragrance | 0.25%–0.65% |
| Hydroxypropyl Methylcellulose | 0.2–0.5% |
| Selenium Sulfide | .9–1.1% |
| Sodium Citrate | 0–0.1% |
| Water | to 100.0% |

4. An anti-dandruff shampoo with conditioner with a pH value less than or equal to 6.5 comprising by weight about:

| INGREDIENT | CONCENTRATION BY WEIGHT |
| --- | --- |
| Ammonium Lauryl Ether Sulfate | 15.0% |
| Ammonium Lauryl Sulfate | 50.0% |
| Citric Acid | 0.13% |
| Cocamide DEA | 1.0% |
| Dimethicone | 0.5% |
| Di(Hydrogentated) Tallow Phthalic Acid Amide | 5.0% |
| DMDM Hydantoin | 0.2% |
| Fragrance | 0.5% |
| Hydroxypropyl Methylcellulose | 0.3% |
| Selenium Sulfide | 1.0% |
| Sodium Citrate | 0.04% |
| Water | to 100.0% |

5. An anti-dandruff shampoo with conditioner according to claim 1 wherein said selenium sulfide is present at a level of about 0.5% to about 2.5% by weight.

6. An anti-dandruff shampoo with conditioner according to claim 1 wherein said selenium sulfide is present at a level of about 0.8% to about 1.5% by weight.

7. An anti-dandruff shampoo with conditioner according to claim 1 wherein said selenium sulfide is present at a level of about 1.0by weight.

8. An anti-dandruff shampoo with conditioner according to claim 1 wherein said buffer system is comprised of sodium citrate and citric acid.

* * * * *